United States Patent
Donnerhacke et al.

(10) Patent No.: US 7,364,299 B2
(45) Date of Patent: Apr. 29, 2008

(54) INTEGRAL APPARATUS FOR TESTING TWILIGHT VISION AND GLARE SENSITIVITY AND A METHOD FOR OPERATING THE APPARATUS

(75) Inventors: Karl-Heinz Donnerhacke, Jena (DE); Manfred Dick, Gefell (DE)

(73) Assignee: Carl Zeiss Jena GmbH, Jena (DE)

( * ) Notice: Subject to any disclaimer, the term of this patent is extended or adjusted under 35 U.S.C. 154(b) by 64 days.

(21) Appl. No.: 11/328,506

(22) Filed: Jan. 9, 2006

(65) Prior Publication Data
US 2006/0238704 A1    Oct. 26, 2006

Related U.S. Application Data

(63) Continuation-in-part of application No. PCT/EP2004/007266, filed on Jul. 3, 2004.

(30) Foreign Application Priority Data
Jul. 8, 2003    (DE) ............... 103 31 592

(51) Int. Cl.
*A61B 3/02* (2006.01)
*A61B 3/10* (2006.01)

(52) U.S. Cl. .................. 351/222; 351/205

(58) Field of Classification Search .......... 351/205, 351/208, 211, 216, 221, 237, 239, 243–244
See application file for complete search history.

(56) References Cited

U.S. PATENT DOCUMENTS

| | | | | |
|---|---|---|---|---|
| 4,155,632 A | * | 5/1979 | Wolbarsht | 351/243 |
| 5,675,399 A | * | 10/1997 | Kohayakawa | 351/237 |
| 5,870,168 A | * | 2/1999 | Kirchhuebel et al. | 351/221 |
| 5,963,300 A | | 10/1999 | Horwitz | |
| 2002/0140902 A1 | | 10/2002 | Guirao et al. | |
| 2003/0147048 A1 | * | 8/2003 | Mihashi | 351/211 |
| 2004/0105073 A1 | * | 6/2004 | Maddalena et al. | 351/205 |
| 2004/0156015 A1 | * | 8/2004 | Campbell | 351/205 |

FOREIGN PATENT DOCUMENTS

| | | |
|---|---|---|
| CA | 2438109 A1 | 8/2002 |
| DE | 19641632 A1 | 5/1997 |
| DE | 19649542 A1 | 4/1998 |
| EP | 1366706 A1 | 12/2003 |
| WO | WO01/21062 A1 | 3/2001 |
| WO | WO01/82791 A1 | 11/2001 |
| WO | WO02/083078 A2 | 10/2002 |

* cited by examiner

*Primary Examiner*—Scott J. Sugarman
*Assistant Examiner*—DaWayne A Pinkney
(74) *Attorney, Agent, or Firm*—Nils H. Ljungman & Associates

(57) ABSTRACT

An integral apparatus for testing twilight vision and glare sensitivity and a method for operating the apparatus. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 3 Drawing Sheets

INTEGRAL APPARATUS FOR TESTING TWILIGHT VISION AND GLARE SENSITIVITY AND A METHOD FOR OPERATING THE APPARATUS

CONTINUING APPLICATION DATA

This application is a Continuation-In-Part application of International Patent Application No. PCT/EP2004/007266, filed on Jul. 3, 2004, which claims priority from Federal Republic of Germany Patent Application No. 103 31 592.6, filed on Jul. 8, 2003. International Patent Application No. PCT/EP2004/007266 was pending as of the filing date of this application. The United States was an elected state in International Patent Application No. PCT/EP2004/007266.

BACKGROUND

Twilight vision (mesopic vision) is the term for a combination between photopic vision and scotopic vision in low but not quite dark lighting situations. This range comprises ambient brightness from approximately 32 to 0.0032 candlepower per square meter (cd/m2). In traffic, this range of brightness occurs at dusk and at night in the headlights of a motor vehicle.

In twilight vision, visual perception is not as good as in daylight vision. The primary difference is an increase in the threshold of perceivable contrast. The principal causes are higher-order visual defects (aberrations) which have an adverse effect on the ability to see contrast as the diameter of the pupil increases as the ambient brightness decreases.

Mesopic contrast visual acuity is one of the critical visual abilities, especially in traffic. In contrast to daylight visual acuity, which is tested under high contrast conditions, at night, larger structures with lower contrast play the more important role. The measurement of mesopic contrast acuity is a complex determination of visual acuity and sensitivity to contrast, during which only the contrast is varied. The contrast threshold identified is called "twilight visual acuity".

The methods for the determination of mesopic contrast visual acuity with and without glare were originally developed to check the visual acuity that a driver must have for night driving. However, the examinations also yield diagnostic information on the transparency of the refractive media on one hand and the neuronal visual functions on the other hand (diabetic retinopathy, AMD, glaucoma) and are currently of major importance for a comprehensive evaluation of the quality of vision and after refractive surgical interventions.

On the appliances of the prior art for the examination of the mesopic contrast visual acuity (twilight vision) and glare sensitivity such as contrastometers (manufactured by BKG Medizintechnik, Bayreuth), Mesotest II (manufactured by Oculus Optikgeräte, Wetzlar) and Nyktometer 500 (manufactured by Rodenstock Instrumente, Ottobrunn), with defined ambient lighting (for photopic vision at 85 cd/m2, for contrast vision sensitivity 0.032 cd/m2, for glare sensitivity 0.1 cd/m2) test patterns with different contrast conditions are offered which the test subject must recognize. The visual acuity at the respective ambient brightness is determined from the smallest size the patient can still recognize.

In addition, the influences on mesopic visual function are many and range from lighting conditions to optics to the quality of the ocular media and health of the retina, as well as by the optical properties of the eye, such as pupil size.

Understanding the relationship between pupil size and visual function is crucial to surgeons' ability to manage patients' expectations preoperatively, such as during laser in-situ keratomileusis (LASIK) treatment. Generally, large pupils worsen mesopic vision if significant aberrations, especially spherical aberration, are present. Minimizing the amount of induced spherical aberrations can improve mesopic function. Second, glare and mesopic visual complaints increase when a patient has residual refractive error, regardless of pupil size. Larger pupils aggravate the problem, however. For more than a century, ophthalmologists have been aware that defocus depends on pupil size and the location of aberrations on the cornea. When pupils dilate in dim lighting, aberrations induced by refractive surgery that are located in the midperiphery are able to enter the visual system and can worsen visual function.

Therefore, it is important to accurately test mesopic vision prior to LASIK treatments or any other type of treatment in order to better prepare the surgeon for the appropriate treatment approach, as well as to counsel the patient on possible outcomes and effects of the treatment.

In addition, it would be advantageous to combine such testing, and the data obtained therefrom, with the use of adaptive optics. Originally developed to perfect images taken from telescopes, adaptive optics can provide extremely detailed data for use in cornea sculpting.

Adaptive optics, in general, uses wavefront sensing. A wavefront can be thought of as a group of waves traveling through space, so that their combined "front" is a surface. In a planar wavefront, the waves travel in the same direction at the same rate. Images represented with a planar wavefront can be moved from one place to another. If the waves do not fly straight and true to each other, the image represented will not look the same upon arrival. As images come through the atmosphere and into optical elements, such as high-powered telescopes, planar wavefronts are slightly deformed. To compensate for this, sensitive detection systems were devised to quantify wavefront deformation. Astronomers coupled these systems with tunable mirrors, thereby introducing opposing wavefront deformations. These wavefront-sensing components allow the system to adapt to wavefront deformations.

In examining the eye, flat wavefronts from laser sources are sent through the cornea toward the retina. Some of the light bounces off the retina and exits the eye. An array of lenses collects the reflected light so that a sensitive detector can determine the directionality of the beams comprising the wavefront. The data relayed by the detector is quantified and enables a doctor or surgeon to develop an appropriate approach for treatment, such as by corrective lenses or surgery.

OBJECT OR OBJECTS

The object of the invention is a method and its apparatus for the determination of objective parameters for the visual function of the human eye at defined ambient brightness levels. It is a further object of the application to describe a method and apparatus for combining the mesopic vision testing with adaptive optics to essentially simultaneously determine a subject's mesopic vision and examine the subject's eyes for aberrations in an efficient and streamlined fashion.

SUMMARY

The invention teaches that this object is accomplished by the features disclosed in the independent claims. Preferred developments of the invention are described in the dependent claims. The method and the apparatus taught by the invention make it possible, under defined ambient brightness levels, to measure the parameters of visual function and simultaneously to measure the dilation of the pupil that occurs at defined ambient brightness and the aberrations of the eye.

Consequently, an objective assessment of the effect of higher-order visual deficiencies (aberrations) on the quality of vision becomes possible. Visual deficiencies or aberrations include astigmatism, coma, spherical aberration, trefoil, and other aberrations. Also, defocus, myopia, hyperopia, and presbyopia can be determined.

In addition to the comprehensive characterization of quality of vision, the method and the apparatus also make possible follow-up measurements in which the measured aberrations are compensated by suitable measures.

In one particularly preferred variant of the invention, for the compensation of the higher-order aberrations that are measured (i.e. on each side of sphere and cylinder)—which are strictly associated with the dilation of the pupil as a function of the ambient brightness—suitable optical means (phase plate, adaptive optical elements that are swung in and out), and under these conditions a measurement of the visual function can be carried out.

The determination of the quality of vision with compensated aberrations is important for advising the patient and planning refractive surgical interventions (preview function), and also makes possible a selective diagnosis of disruptions of neuronal visual functions.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

Figure 1:
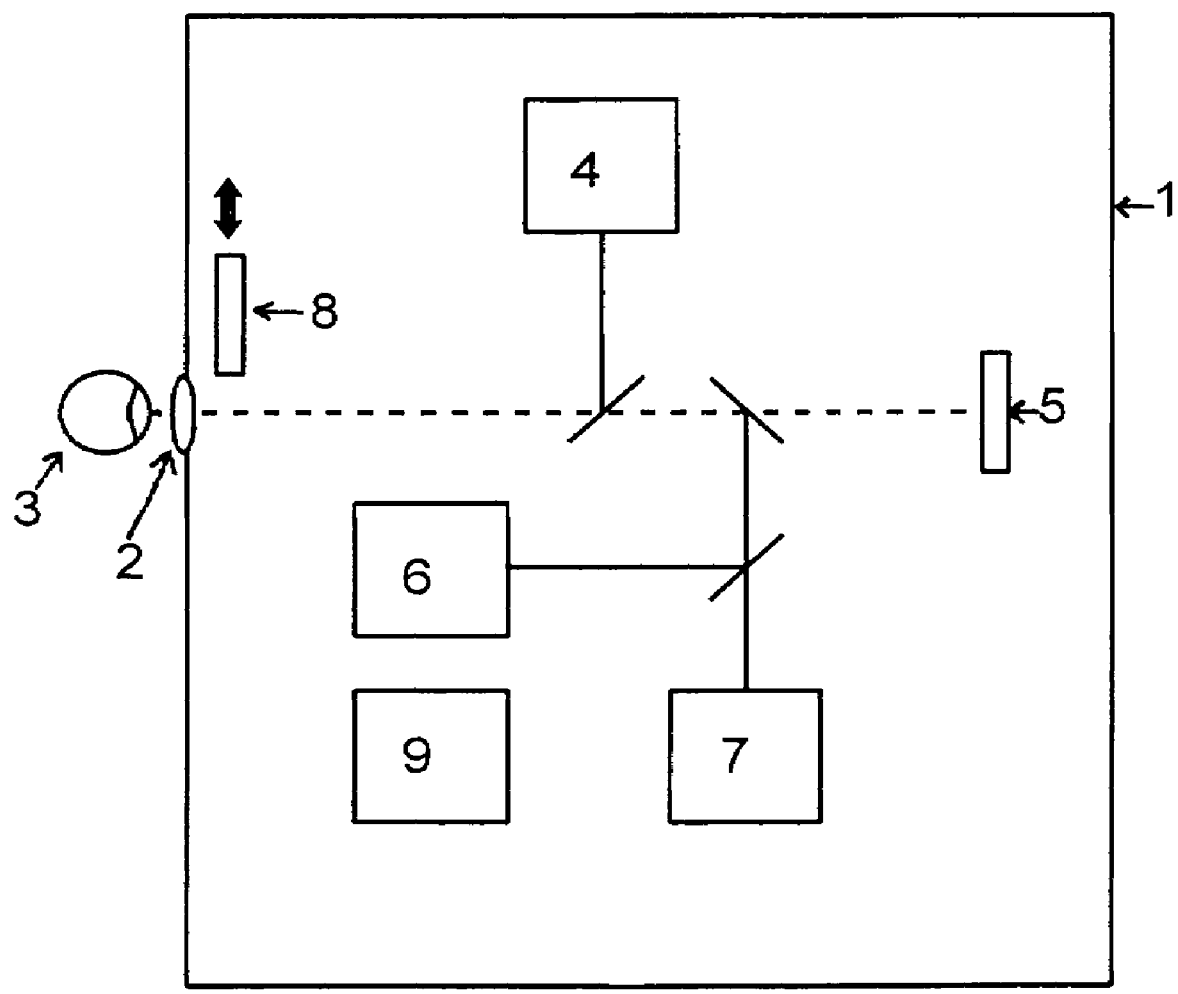
FIG. 1 is a schematic illustration of one possible embodiment of an eye examination apparatus or appliance.

The apparatus is surrounded by a light-tight enclosure (1) which has a monocular or preferably binocular eyepiece (2) for the examination of the patient's eye(s) (3). The illumination device (4) is used to control and adjust a defined brightness.

Under different freely selectable illumination conditions, the subject's eye or eyes are subjected to a vision test at different contrast conditions (5) to check visual function.

Using the measurement system (6) and (7), the pupil diameter (6) and the aberrations (7) of the eye are measured at the defined ambient illumination that has been set. A unit of this type for the determination of the pupil diameter (6) is, in itself, described in the prior art, and can be designed and operated as described in, for example, DE 196 41 632 and corresponding U.S. Pat. No. 5,822,033, or DE 196 49 542 (whereby reference is made to the entire disclosure of these prior art documents). The apparatus (7) for the determination of the aberrations of the eye can be, for example, a Hartmann-Shack wave-front sensor. The principle is described in, among other sources, Liang et al., "Objective Measurement of Wave Aberrations of the Human Eye with the use of a Hartmann-Shack Wave-Front Sensor," J. Opt. Soc. Am. A., Vol. 11, No. 7, pp. 1949-1957, (July 1994), whereby reference is also made to the entire disclosure of these prior art documents. Likewise, the apparatus (7) for the determination of the aberrations of the eye can be an aberrometer, e.g. of the type manufactured as WASCA by the firm Carl Zeiss Meditec AG. By means of one or more compensators (8), defects in the optical system of the eye can be corrected to make it possible to measure visual acuity at different corrections. The optical compensators can be simple optical elements (lenses), special phase plates and/or adaptive optical elements. In the latter case, the output signal of the unit for the determination of the pupil diameter (6) and of the aberrations (7) is fed to a computer and control unit (9) which, from the data, delivers the control data for the control of an adaptive optical compensator and thereby makes possible a correction of the effect of the measured aberrations.

The computer and control unit (9) is also responsible for controlling the entire sequence of actions and operations of the overall apparatus and its sub-functions, as well as for the measurement, processing, presentation and output of the measurement data, and also makes possible data communications with external systems.

The determination of the visual acuity with compensated aberrations is of major importance for advising the patient and planning refractive surgical interventions (preview function). Measurements of this type also make it possible to distinguish between deficiencies (aberrations) of optical origin in the front portion of the eye and changes caused by disease in the rear portion of the eye (diabetic retinopathy, age-related macular degeneration, glaucoma) and thereby facilitates the selective diagnosis of deficiencies of neuronal visual functions.

Treatment time can be reduced by the joint measurement of visual acuities and the objective physical conditions for the achievement of these acuities. The quality of the examination results is improved by the related effective and loss-free linkage of the measurement data.

Figure 2:
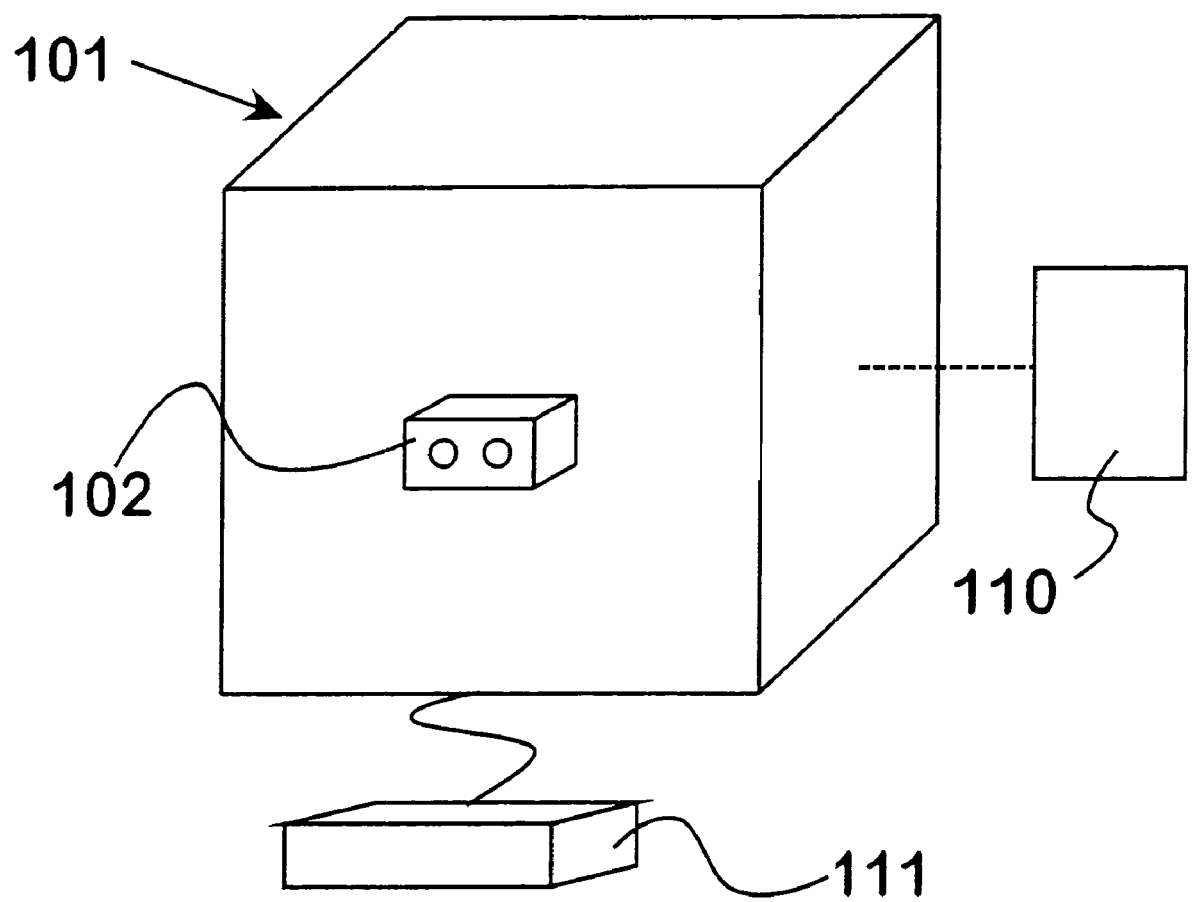
FIG. 2 shows another possible embodiment of an eye examination and twilight or mesopic vision testing apparatus or appliance.

FIG. 2 shows another possible embodiment of an eye examination and twilight or mesopic vision testing apparatus or appliance. The apparatus has a substantially box-shaped, light-tight enclosure 101. There is a binocular eyepiece 102 through which the patient or subject looks during examination, which eyepiece in at least one other possible embodiment could be monocular. The components of the apparatus located inside the enclosure 101 are not shown, but could be, in at least one possible embodiment, similar to those shown in the schematic illustrations of FIGS. 1 and 3. In addition, the apparatus has an interface 110 for use by an operator of the apparatus, such as a doctor or technician conducting the examination. This interface could be in the form of a keypad or touchscreen or other suitable input device. Through this interface the operator can, in at least one possible embodiment, control and/or monitor the testing parameters and any pertinent data generated by the testing. In the embodiment shown in FIG. 2, there is also a patient interface 111, which could also be in the form of a keypad or touch screen or other suitable input device. In this embodiment, the patient can modify at least some of the testing parameters by inputting commands to the apparatus. Such an embodiment could provide interactive testing that enables the patient to assist the doctor or technician in more quickly determining appropriate corrective data.

It should be understood that FIG. 2 shows a possible embodiment, and should not be considered as limiting the scope of all embodiments disclosed in this application. For example, either or both of the interfaces 110, 111 could be omitted from an embodiment and replaced by an entirely automated system that conducts a battery of preprogrammed tests absent of control by a doctor, technician, or patient. Further, the box shape and size of the enclosure 101, as well as the size and location of the eyepiece 102 are shown for one possible embodiment, and variations thereof are within the scope of this application.

Figure 3:
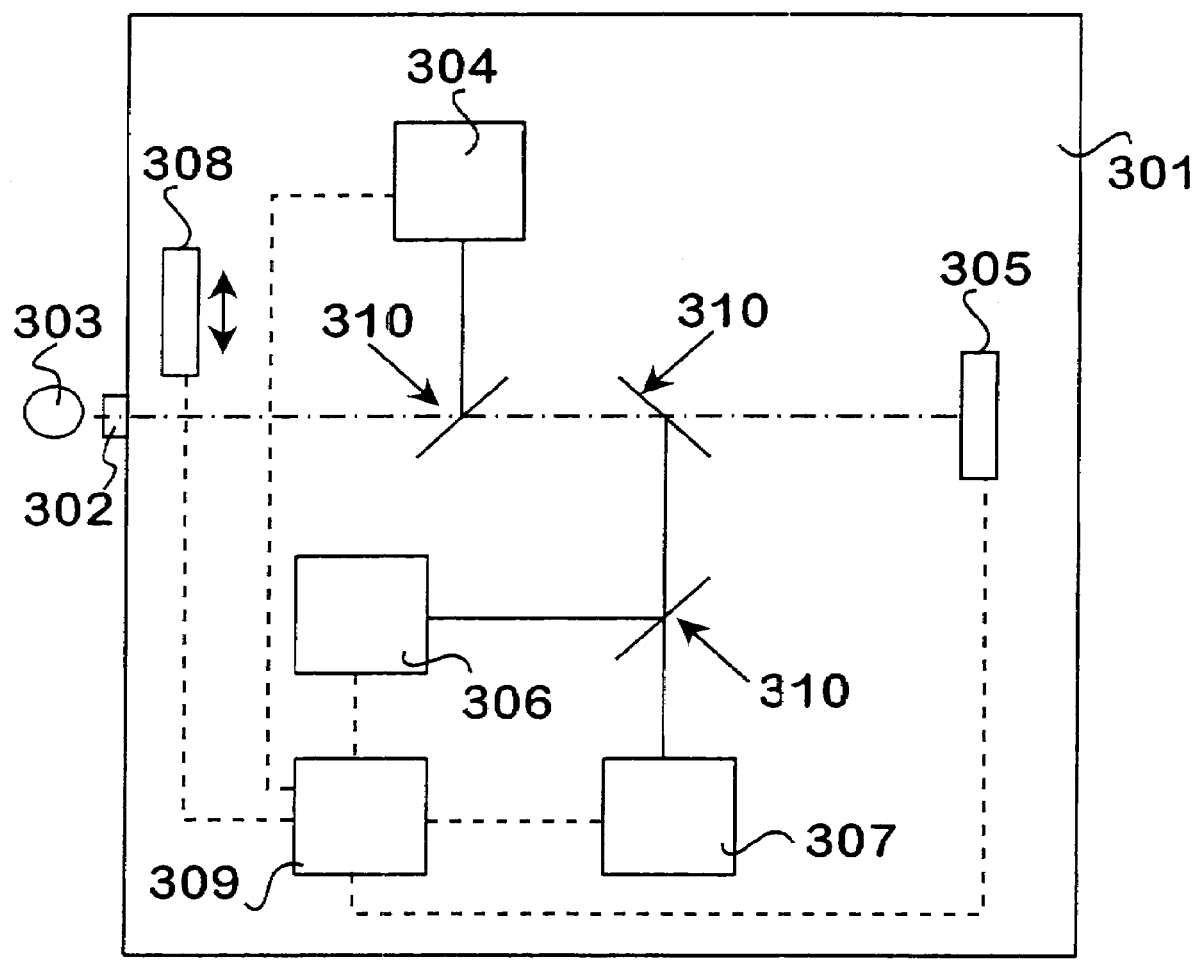
FIG. 3 shows a schematic illustration of another possible embodiment of an eye examination and twilight or mesopic vision testing apparatus or appliance.

FIG. 3 shows a schematic illustration of another possible embodiment of an eye examination and twilight or mesopic vision testing apparatus or appliance. FIG. 3 shows that the apparatus is surrounded by a light-tight enclosure 301 which has a monocular or binocular eyepiece 302 for the examination of a patient's eye(s) 303. An illumination device 304 is used to control and adjust a defined brightness. The illumination device 304 projects light beams of varying brightness onto a half mirror 310. The half mirror has a reflective surface on one side that reflects the projected light from the illumination device 304 toward the patient's eye(s). The other non-reflective side of the half mirror permits the image 305 to be viewed by the patient.

Under different freely selectable illumination conditions, the subject's eye or eyes are subjected to a vision test on an image 305 at different contrast conditions to check visual function. The image 305 could be a standard black and white eye chart, a color eye chart, or a picture. These images 305 could be shown on a printed sheet or a computer monitor.

Using the measurement system 306 and 307, the pupil diameter and the aberrations of the eye are measured at the defined ambient illumination that has been set. A unit 306 of this type for the determination of the pupil diameter is, in itself, described in the prior art, and can be designed and operated as described in, for example, DE 196 41 632 and corresponding U.S. Pat. No. 5,822,033, or DE 196 49 542 (whereby reference is made to the entire disclosure of these prior art documents). The apparatus 307 for the determination of the aberrations of the eye can be, for example, a Hartmann-Shack wave-front sensor. The principle is described in, among other sources, Liang et al., "Objective Measurement of Wave Aberrations of the Human Eye with the use of a Hartmann-Shack Wave-Front Sensor," J. Opt. Soc. Am. A., Vol. 11, No. 7, pp. 1949-1957, (July 1994), whereby reference is also made to the entire disclosure of these prior art documents. Likewise, the apparatus 307 for the determination of the aberrations of the eye can be an aberrometer, e.g. of the type manufactured as WASCA by the firm Carl Zeiss Meditec AG. By means of one or more compensators 308, defects in the optical system of the eye can be corrected to make it possible to measure visual acuity at different corrections. The optical compensators can be simple optical elements (lenses), special phase plates and/or adaptive optical elements. In the latter case, the output signal of the unit 306 for the determination of the pupil diameter and of the aberrations 307 is fed to a computer and control unit 309 which, from the data, delivers the control data for the control of an adaptive optical compensator and thereby makes possible a correction of the effect of the measured aberrations.

The computer and control unit 309 is also responsible for controlling the entire sequence of actions and operations of the overall apparatus and its sub-functions, as well as for the measurement, processing, presentation and output of the measurement data, and also makes possible data communications with external systems. The control unit 309, in at least one possible embodiment, is connected to each device 304, 305, 306, 307, 308 in the apparatus to permit control of these devices to permit flexibility in the examination and testing. The computer control unit 309 could be fully automated and self-controlled, in at least one possible embodiment, or it could be connected to at least one external control device, such as shown in FIG. 2.

The realization of the invention is not restricted to the illustrated exemplary embodiment. A technician skilled in the art will be able to devise developments that do not go beyond the scope of protection of the claims.

This application relates to an eye examining appliance for characterizing the visual function of the eye. The appliance comprises a device for determining the visual acuity in twilight or half-light and/or sensitivity to dazzling, and a device for determining the diameter of the pupil and/or the aberrations of the eye.

One feature or aspect of an embodiment is believed at the time of the filing of this patent application to possibly reside broadly in a method for the characterization of the visual function of the eye at different ambient brightness, characterized in that under essentially defined conditions of ambient brightness, in addition to parameters of visual function and/or contrast visual acuity and/or glare sensitivity, other parameters that determine visual function, such as pupil width and/or the aberrations of the eye, are measured, preferably simultaneously.

Another feature or aspect of an embodiment is believed at the time of the filing of this patent application to possibly reside broadly in a method for the characterization of visual function, whereby corresponding corrective lenses are interposed to compensate for existing visual deficiencies (sphere, cylinder).

Yet another feature or aspect of an embodiment is believed at the time of the filing of this patent application to possibly reside broadly in a method for the characterization of visual function, whereby minus lenses are interposed to compensate for any night myopia.

Still another feature or aspect of an embodiment is believed at the time of the filing of this patent application to possibly reside broadly in a method for the characterization of visual function, whereby suitable optical means (phase plate, adaptive optical elements) are pivoted in and out before or during the measurement of visual function to compensate for higher-order aberrations measured.

A further feature or aspect of an embodiment is believed at the time of the filing of this patent application to possibly reside broadly in an eye examination appliance for the characterization of the visual function of the eye, which has an apparatus for the determination of acuity of twilight vision and/or sensitivity to glare, as well as an apparatus for the determination of the pupil diameter and/or of the aberrations of the eye.

Another feature or aspect of an embodiment is believed at the time of the filing of this patent application to possibly reside broadly in an integral apparatus for testing visual acuity, contrast visual acuity, and glare sensitivity, and for at least one of: measuring pupil size and determining aberrations of the eye, said apparatus being configured to substantially simultaneously perform at least two of: testing visual acuity, testing contrast visual acuity, testing glare sensitivity, and at least one of: measuring pupil size and determining aberrations of the eye, said apparatus comprising: a housing structure being configured to essentially prevent penetration by light into the interior of said housing structure; an eyepiece being connected to said housing structure; said eyepiece being configured and disposed to permit viewing of the interior of said housing structure by a patient; testing components being disposed within said housing structure, said testing components comprising: a test image arrangement being configured and disposed to provide a test image to be viewed by the patient through said eyepiece; an illumination device being configured and disposed to project light to produce apparent varying levels of ambient light in at least one eye of the patient; a monitoring and measuring arrangement being configured and disposed to monitor and measure at least one of: pupil size of the at least one eye of the patient and aberrations of the at least one eye of the patient; and a computer control device being configured and disposed to control at least one of: said test image arrangement, said illumination device, and said monitoring and measuring arrangement.

Yet another feature or aspect of an embodiment is believed at the time of the filing of this patent application to possibly reside broadly in an apparatus, wherein said apparatus comprises a movable corrective arrangement configured to be interposed between the test image and the at least one eye of the patient to compensate for existing visual deficiencies that are measured on each side of sphere and cylinder of the at least one eye.

Still another feature or aspect of an embodiment is believed at the time of the filing of this patent application to possibly reside broadly in an apparatus, wherein said movable corrective arrangement comprises at least one of: minus lenses to compensate for any night myopia; and optical elements configured to be pivoted in and out before or during the measurement of visual function to compensate for higher-order aberrations measured; and said optical elements comprise at least one of: phase plates and adaptive optical elements; said apparatus comprises an eyepiece connected to said housing structure; said eyepiece is configured and disposed to permit viewing of the interior of said housing structure by the patient; and said control device comprises a computer control device.

A further feature or aspect of an embodiment is believed at the time of the filing of this patent application to possibly reside broadly in a method for testing visual acuity, contrast visual acuity, and glare sensitivity, and for at least one of: measuring pupil size and determining aberrations of the eye, using an integral apparatus being configured to substantially simultaneously perform at least two of: testing visual acuity, testing contrast visual acuity, testing glare sensitivity, and at least one of: measuring pupil size and determining aberrations of the eye, said apparatus comprising: a housing structure being configured to essentially prevent penetration by light into the interior of said housing structure; an eyepiece being connected to said housing structure; said eyepiece being configured and disposed to permit viewing of the interior of said housing structure by a patient; testing components being disposed within said housing structure, said testing components comprising: a test image arrangement being configured and disposed to provide a test image to be viewed by the patient through said eyepiece; an illumination device being configured and disposed to project light to produce apparent varying levels of ambient light in at least one eye of the patient; a monitoring and measuring arrangement being configured and disposed to monitor and measure at least one of: pupil size of the at least one eye of the patient and aberrations of the at least one eye of the patient; and a computer control device being configured and disposed to control at least one of: said test image arrangement, said illumination device, and said monitoring and measuring arrangement, said method comprising the steps of: producing an image to be viewed by a patient through an eyepiece; projecting light to produce apparent varying levels of ambient light in at least one eye of the patient; monitoring and measuring at least one of: pupil size of the at least one eye of the patient and aberrations of the at least one eye of the patient; and substantially simultaneously performing, for at least one eye of the patient, at least two of: testing visual acuity, testing contrast visual acuity, testing glare sensitivity, and at least one of: measuring pupil size and determining aberrations of the at least one eye of the patient.

Another feature or aspect of an embodiment is believed at the time of the filing of this patent application to possibly reside broadly in a method, wherein said apparatus comprises a movable corrective arrangement configured to be interposed between the test image and the at least one eye of the patient to compensate for existing visual deficiencies that are measured on each side of sphere and cylinder of the at least one eye, and said method further comprises the step of: interposing a movable corrective arrangement between the test image and the at least one eye of the patient to compensate for existing visual deficiencies that are measured on each side of sphere and cylinder of the at least one eye.

Yet another feature or aspect of an embodiment is believed at the time of the filing of this patent application to possibly reside broadly in a method, wherein said movable corrective arrangement comprises minus lenses to compensate for any night myopia, and said method further comprises the step of: interposing minus lenses between the test image and the at least one eye of the patient to compensate for any night myopia.

Still another feature or aspect of an embodiment is believed at the time of the filing of this patent application to possibly reside broadly in a method, wherein said movable corrective arrangement comprises optical elements configured to be pivoted in and out before or during the measurement of visual function to compensate for higher-order aberrations measured; and said optical elements comprise at least one of: phase plates and adaptive optical elements, and said method further comprises the step of: interposing optical elements between the test image and the at least one eye of the patient before or during the measurement of visual function to compensate for higher-order aberrations measured.

A further feature or aspect of an embodiment is believed at the time of the filing of this patent application to possibly reside broadly in an integral apparatus for testing visual acuity, contrast visual acuity, and glare sensitivity, and for at least one of: measuring pupil size and determining aberrations of the eye, said apparatus being configured to substantially simultaneously perform at least two of: testing visual acuity, testing contrast visual acuity, testing glare sensitivity, and at least one of: measuring pupil size and determining aberrations of the eye, said apparatus comprising: a housing structure being configured to essentially prevent penetration by light into the interior of said housing structure; testing components being disposed within said housing structure, said testing components comprising: a test image arrangement being configured and disposed to provide a test image to be viewed by a patient; an illumination device being configured and disposed to project light to produce apparent varying levels of ambient light in at least one eye of the patient; a monitoring and measuring arrangement being configured and disposed to monitor and measure at least one of: pupil size of the at least one eye of the patient and aberrations of the at least one eye of the patient; and a control device being configured and disposed to control at least one of: said test image arrangement, said illumination device, and said monitoring and measuring arrangement.

Another feature or aspect of an embodiment is believed at the time of the filing of this patent application to possibly reside broadly in a method for testing visual acuity, contrast visual acuity, and glare sensitivity, and for at least one of: measuring pupil size and determining aberrations of the eye, using an integral apparatus being configured to substantially simultaneously perform at least two of: testing visual acuity, testing contrast visual acuity, testing glare sensitivity, and at least one of: measuring pupil size and determining aberrations of the eye, said apparatus comprising: a housing structure being configured to essentially prevent penetration by light into the interior of said housing structure; testing components being disposed within said housing structure, said testing components comprising: a test image arrangement being configured and disposed to provide a test image to be viewed by a patient; an illumination device being configured and disposed to project light to produce apparent varying levels of ambient light in at least one eye of the patient; a monitoring and measuring arrangement being configured and disposed to monitor and measure at least one of: pupil size of the at least one eye of the patient and aberrations of the at least one eye of the patient; and a control device being configured and disposed to control at least one of: said test image arrangement, said illumination device, and said monitoring and measuring arrangement, said method comprising the steps of: producing an image to be viewed by a patient; projecting light to produce apparent varying levels of ambient light in at least one eye of the patient; monitoring and measuring at least one of: pupil size of the at least one eye of the patient and aberrations of the at least one eye of the patient; and substantially simultaneously performing, for at least one eye of the patient, at least two of: testing visual acuity, testing contrast visual acuity, testing glare sensitivity, and at least one of: measuring pupil size and determining aberrations of the at least one eye of the patient.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of illumination devices, components thereof, and components associated therewith, which may possibly be utilized or adapted for use in at least one possible embodiment of the present invention, may possibly be found in the following U.S. patents: U.S. Pat. No. 6,142,659, entitled "Optical Illumination device;" U.S. Pat. No. 6,761,457, entitled "Optical illumination device and projection display device;" U.S. Pat. No. 6,913,373, entitled "Optical illumination device exposure device and exposure method;" and U.S. Pat. No. 5,918,974, entitled "Optical illumination device."

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of vision testing devices, components thereof, and components associated therewith, which may possibly be utilized or adapted for use in at least one possible embodiment of the present invention, may possibly be found in the following U.S. patents: U.S. Pat. No. 6,715,878, entitled "Apparatus for measuring visual performance;" U.S. Pat. No. 4,412,729, entitled "Vision testing device;" U.S. Pat. No. 6,379,007, entitled "Eye chart with distinct symbols and methods for vision testing;" U.S. Pat. No. 5,801,809, entitled "Eye chart with colour vision screening;" U.S. Pat. No. 5,870,168, entitled "Vision-testing device;" and U.S. Pat. No. 5,216,458, entitled "Apparatus and method for testing visual acuity and contrast sensitivity."

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of wave front sensors, adaptive optics systems, and aberrometers, components thereof, and components associated therewith, which may possibly be utilized or adapted for use in at least one possible embodiment of the present invention, may possibly be found in the following U.S. patents: U.S. Pat. No. 6,739,721, entitled "Method and apparatus for calibrating and certifying accuracy of a wavefront sensing device;" U.S. Pat. No. 6,736,509, entitled "Aberrometer illumination apparatus and method;" U.S. Pat. No. 6,637,884, entitled "Aberrometer calibration;" U.S. Pat. No. 6,396,588, entitled "Hybrid curvature-tilt wave front sensor;" U.S. Pat. No. 5,294,971, entitled "Wave front sensor;" U.S. Pat. No. 4,490,039, entitled "Wave front sensor;" U.S. Pat. No. 6,595,642 entitled "Ophthalmic instrument having Hartmann wavefront sensor with extended source;" U.S. Pat. No. 6,932,475, entitled "Device for measuring aberration refraction of the eye;" U.S. Pat. No. 4,650,302, entitled "Interferometric eye test method and apparatus;" and U.S. Pat. No. 6,827,444, entitled "Rapid, automatic measurement of the eye's wave aberration."

All of the patents, patent applications and publications recited herein, and in the Declaration attached hereto, are hereby incorporated by reference as if set forth in their entirety herein.

Some examples of transmissive or reflective elements, components thereof, and components associated therewith, which may possibly be utilized or adapted for use in at least one possible embodiment of the present invention, may possibly be found in the following U.S. patents: U.S. Pat. No. 6,426,933, entitled "Optical pickup apparatus having polarizing phase plates;" U.S. Pat. No. 6,860,603, entitled "Best corrected visual acuity characteristics measuring device, best corrected visual acuity characteristics measuring method, contrast sensitivity measuring device, contrast sensitivity measuring method, and contrast sensitivity target displaying device;" and U.S. Pat. No. 6,406,147, entitled "Visual acuity testing apparatus."

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

Some examples of half mirrors and systems or devices including or using half mirrors, components thereof, and components associated therewith, which may possibly be utilized or adapted for use in at least one possible embodiment of the present invention, may possibly be found in the following U.S. patents: U.S. Pat. No. 6,980,506, entitled "Pickup apparatus for disk player having a frame for supporting a half-mirror"; U.S. Pat. No. 6,968,640, entitled "Half mirror reflector having LED road sign"; U.S. Pat. No. 6,961,089, entitled "Digital camera that displays a previously captured image on an LCD when a half-mirror is in motion"; U.S. Pat. No. 6,928,044, entitled "Apparatus for fixing half mirror of optical pickup"; U.S. Pat. No. 6,909,688, entitled "Optical pickup for fixing a half mirror to a predetermined position"; U.S. Pat. No. 6,903,512, entitled "Half mirror film producing method and optical element comprising a half mirror film"; U.S. Pat. No. 6,556,350, entitled "Half mirror"; U.S. Pat. No. 6,542,297, entitled "Half mirror varying apparatus for three-dimensional image displaying apparatus"; U.S. Pat. No. 6,091,545, entitled "Real image finder optical system having half mirror and information display surface within eyepiece optical system"; U.S. Pat. No. 5,938,311, entitled "Half mirror display device for instruments with improved illumination system"; U.S. Pat. No. 5,721,586, entitled "Movable half mirror having a movable prompter for TV camera"; U.S. Pat. No. 5,663,944, entitled "Vertical cavity laser light beam monitored by reflection of a half mirror, with application in optical pickup"; U.S. Pat. No. 5,596,360, entitled "Image reading apparatus with a half mirror"; U.S. Pat. No. 5,198,930, entitled "Wide-band half-mirror"; U.S. Pat. No. 4,979,802, entitled "Synthetic resin half-mirror"; and U.S. Pat. No. 4,368,950, entitled "Image observation device having glass piled half mirror".

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Oct. 6, 2004, and/or cited elsewhere are hereby incorporated by reference as if set forth in their entirety herein as follows: CA 2438109, published Aug. 15, 2002, having inventors Mihashi et al.; WO 02083078, published Oct. 24, 2002, having inventors Wakil et al.; US 2002140902, published Oct. 3, 2002, having inventors Guirao et al.; and US 5963300, published Oct. 5, 1999, having inventor Horwitz.

The corresponding foreign and international patent publication applications, namely, Federal Republic of Germany Patent Application No. 103 31 592.6, filed on Jul. 8, 2003, having inventors Karl-Heinz DONNERHACKE and Manfred DICK, and DE-OS 103 31 592.6 and DE-PS 103 31 592.6, and International Application No. PCT/EP2004/007266, filed on Jul. 3, 2004, having WIPO Publication No. WO2005/004706 and inventors Karl-Heinz DONNERHACKE and Manfred DICK, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

U.S. Pat. No. 6,722,767 issued to Apr. 20, 2004 is hereby incorporated by reference as if set forth in its entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of examining visual functions of at least one eye of a patient, said method comprising the steps of:
   providing an image to be viewed by the patient;
   projecting light at a first brightness level in the at least one eye of the patient;
   monitoring and measuring a first pupil size at said first brightness level and detecting aberrations at the first pupil size, said aberrations comprising: spherical aberrations, cylindrical aberrations, and higher-order aberrations;
   using a corrective arrangement comprising:
      adaptive optical elements to correct for refractive errors due to detected higher-order aberrations; and
      corrective lenses to correct for refractive errors due to at least one of: detected spherical aberrations and detected cylindrical aberrations;
   performing subjective testing of visual acuity to verify correction of said refractive errors, and, if correction of said refractive errors is not verified by the patient, further correcting said refractive errors and subjectively testing the visual acuity until correction of said refractive errors is verified by the patient;
   performing at least one of: subjective testing of contrast visual acuity and subjective testing of glare sensitivity; and
   detecting the influence on the visual perception of the patient of at least one of: the transparency of refractive media, including at least the cornea and the intraocular lens, and the neural visual functions, including at least the functions of the macula, of the patient.

2. The method according to claim 1, wherein said method further comprises the steps of:
   projecting light at a second brightness level in the at least one eye of the patient, said second brightness level being different from said first brightness level;
   monitoring and measuring a second pupil size at said second brightness level and detecting aberrations at the second pupil size, said aberrations comprising: spherical aberrations, cylindrical aberrations, and higher-order aberrations;
   using said corrective arrangement to correct for refractive errors due to said detected aberrations at the second pupil size;
   performing subjective testing of visual acuity to verify correction of said refractive errors at the second pupil size and, if correction of said refractive errors is not verified by the patient, further correcting said refractive errors and subjectively testing the visual acuity until correction of said refractive errors is verified by the patient;
   performing at least one of: subjective testing of contrast visual acuity and subjective testing of glare sensitivity at the second pupil size; and
   detecting the influence on the visual perception of the patient of at least one of: the transparency of refractive media and the neural visual functions of the patient at the second pupil size.

3. The method according to claim 2, wherein said method further comprises repeating the steps of providing an image, projecting light, monitoring and measuring pupil size and detecting aberrations, using said corrective arrangement to correct for refractive errors due to said detected aberrations and performing subjective testing of visual acuity, and at least one of: subjective testing of contrast visual acuity and subjective testing of glare sensitivity, and detecting the influence on the visual perception of the patient of at least one of: the transparency of refractive media and the neural visual functions of the patient, as desired to test the patient at varying brightness levels and pupil sizes.

4. A method of examining visual functions of at least one eye of a patient, said method comprising the steps of:
   providing an image to be viewed by the patient;
   providing light at a first brightness level to be perceived by the patient;
   monitoring and measuring a first pupil size at said first brightness level and detecting aberrations at the first pupil size, said aberrations comprising: spherical aberrations, cylindrical aberrations, and higher-order aberrations;
   using a corrective arrangement to correct for refractive errors due to said detected aberrations and performing subjective testing of visual acuity to verify correction of said refractive errors;
   performing at least one of: subjective testing of contrast visual acuity and subjective testing of glare sensitivity; and
   detecting the influence on the visual perception of the patient of at least one of: the transparency of refractive media and the neural visual functions of the patient.

5. The method according to claim 4, wherein said method further comprises the steps of:
- providing light at a second brightness level to be perceived by the patient, said second brightness level being different from said first brightness level;
- monitoring and measuring a second pupil size at said second brightness level and detecting aberrations at the second pupil size, said aberrations comprising: spherical aberrations, cylindrical aberrations, and higher-order aberrations;
- using said corrective arrangement to correct for refractive errors due to said detected aberrations and performing subjective testing of visual acuity to verify correction of said refractive errors at the second pupil size;
- performing at least one of: subjective testing of contrast visual acuity and subjective testing of glare sensitivity at the second pupil size; and
- detecting the influence on the visual perception of the patient of at least one of: the transparency of refractive media and the neural visual functions of the patient at the second pupil size.

6. The method according to claim 5, wherein said method further comprises repeating the steps of providing an image, providing light, monitoring and measuring pupil size and detecting aberrations, using said corrective arrangement to correct for refractive errors due to said detected aberrations and performing subjective testing of visual acuity, and at least one of: subjective testing of contrast visual acuity and subjective testing of glare sensitivity, and detecting the influence on the visual perception of the patient of at least one of: the transparency of refractive media and the neural visual functions of the patient, as desired to test the patient at varying brightness levels and pupil sizes.

7. The method according to claim 6, wherein said corrective arrangement comprises adaptive optical elements.

8. The method according to claim 7, wherein said step of using a corrective arrangement comprises using said adaptive optical elements to correct for refractive errors due to detected higher-order aberrations.

9. The method according to claim 8, wherein said step of using a corrective arrangement comprises positioning said corrective arrangement in front of the at least one eye of the patient.

10. The method according to claim 9, wherein said step of providing light at a brightness level comprises projecting light at a brightness level in the at least one eye of the patient.

11. The method according to claim 10, wherein said corrective arrangement further comprises corrective lenses configured to correct for spherical and cylindrical aberrations, and said step of positioning a corrective arrangement in front of the at least one eye of the patient comprises positioning said corrective lenses in front of the at least one eye of the patient to correct for refractive errors due to detected spherical and cylindrical aberrations.

12. The method according to claim 6, wherein said corrective arrangement further comprises minus lenses configured to correct for night myopia, and said step of using said corrective arrangement comprises positioning minus lenses in front of the at least one eye of the patient to correct for night myopia.

13. The method according to claim 6, wherein said corrective arrangement comprises a phase plate, and said step of using a corrective arrangement comprises positioning said phase plate in front of the at least one eye of the patient to correct for refractive errors due to detected higher-order aberrations.

14. An arrangement for examining visual functions of at least one eye of a patient, said arrangement comprising:
- means for providing an image to be viewed by the patient;
- means for providing light at a brightness level to be perceived by the patient;
- means for monitoring and measuring a pupil size at said brightness level;
- means for detecting aberrations at the pupil size, said aberrations comprising: spherical aberrations, cylindrical aberrations, and higher-order aberrations;
- means for correcting refractive errors due to said detected aberrations;
- means for performing subjective testing of visual acuity to verify correction of said refractive errors; and
- means for performing at least one of: subjective testing of contrast visual acuity and subjective testing of glare sensitivity in order to detect the influence on the visual perception of the patient of at least one of: the transparency of refractive media and the neural visual functions of the patient.

15. The arrangement for examining visual functions according to claim 14, wherein said means for correcting refractive errors comprises adaptive optical elements to correct for refractive errors due to detected higher-order aberrations.

16. The arrangement for examining visual functions according to claim 15, wherein said means for correcting refractive errors comprises corrective lenses to correct for refractive errors due to detected spherical and cylindrical aberrations.

17. The arrangement for examining visual functions according to claim 16, wherein:
- said arrangement comprises a housing structure configured to essentially prevent penetration by light into the interior of said housing structure;
- each of said means for providing an image, said means for providing light, said means for monitoring and measuring pupil size, said means for detecting aberrations, said means for correcting refractive errors, and said means for performing at least one of: subjective testing of contrast visual acuity and subjective testing of glare sensitivity are disposed within said housing; and
- said arrangement comprises a control device being configured and disposed to control at least one of: said means for providing an image, said means for providing light, said means for monitoring and measuring pupil size, said means for detecting aberrations, said means for correcting refractive errors, and said means for performing at least one of: subjective testing of contrast visual acuity and subjective testing of glare sensitivity are disposed within said housing.

18. The arrangement for examining visual functions according to claim 17, wherein said means for correcting refractive errors is configured to be interposed between the test image and the at least one eye of the patient to correct for refractive errors due to said detected aberrations.

19. The arrangement for examining visual functions according to claim 18, wherein:
- said arrangement comprises an eyepiece connected to said housing structure;
- said eyepiece is configured and disposed to permit viewing of the interior of said housing structure by the patient; and
- said control device comprises a computer control device.

20. The arrangement for examining visual functions according to claim 14, wherein said means for correcting refractive errors comprises one of: a phase plate configured to correct for higher-order aberrations, and minus lenses configured to correct for night myopia.

* * * * *

UNITED STATES PATENT AND TRADEMARK OFFICE
CERTIFICATE OF CORRECTION

| | | |
|---|---|---|
| PATENT NO. | : 7,364,299 B2 | Page 1 of 1 |
| APPLICATION NO. | : 11/328506 | |
| DATED | : April 29, 2008 | |
| INVENTOR(S) | : Karl-Heinz Donnerhacke and Manfred Dick | |

It is certified that error appears in the above-identified patent and that said Letters Patent is hereby corrected as shown below:

On the Title page, item 73, after "Assignee:", delete "Carl Zeiss Jena GmbH" and insert --Carl Zeiss Meditec AG--.

Signed and Sealed this

Twenty-eighth Day of October, 2008

JON W. DUDAS
*Director of the United States Patent and Trademark Office*